US007641919B2

(12) United States Patent
Frame

(10) Patent No.: US 7,641,919 B2
(45) Date of Patent: Jan. 5, 2010

(54) ANTI-BACTERIAL PLANT COMPOSITIONS

(75) Inventor: Anne D. Frame, San Juan, PR (US)

(73) Assignee: Inter American University of Puerto Rico, San Juan, PR (US)

( * ) Notice: Subject to any disclaimer, the term of this patent is extended or adjusted under 35 U.S.C. 154(b) by 166 days.

(21) Appl. No.: 10/320,492

(22) Filed: Dec. 17, 2002

(65) Prior Publication Data

US 2003/0152649 A1    Aug. 14, 2003

Related U.S. Application Data

(63) Continuation of application No. PCT/US01/50502, filed on Dec. 28, 2001.

(51) Int. Cl.
*A61K 36/00* (2006.01)
(52) U.S. Cl. ..................................... 424/725
(58) Field of Classification Search ............... None
See application file for complete search history.

(56) References Cited

U.S. PATENT DOCUMENTS

| 4,299,826 | A |   | 11/1981 | Luedders |         |
|-----------|---|---|---------|----------|---------|
| 4,716,120 | A | * | 12/1987 | Tsay et al. | 424/276.1 |
| 5,635,184 | A |   | 6/1997  | Camano   |         |
| 5,884,417 | A | * | 3/1999  | Pare     | 34/263  |
| 6,294,186 | B1| * | 9/2001  | Beerse et al. | 424/405 |

FOREIGN PATENT DOCUMENTS

| EP | 0 499 304 A | 8/1992 |
| JP | 10 298095   | 11/1998 |
| JP | 10 298095 A | 11/1998 |
| JP | 2001 058901 A | 3/2001 |
| WO | WO 96 12467 A | 5/1996 |
| WO | WO 97 16159 A | 5/1997 |
| WO | WO 01 70215 A | 9/2001 |

OTHER PUBLICATIONS

Dixey, R. The Wise Investor; Community Pharmacy Dec. 29, 2000, pp. 1-4 from ProQuest database (accessed Aug. 10, 2005).*
Wickramasinghe M. Bandaranayake, *Xanthones & Triterpenes of Mammea acuminata (Guttiferae)*, Indian Journal of Chemistry, (1980), 19B:463-467.
Anne D. Frame et al., *Antimicrobial Phytochemicals*, P. R. Health Sci. J., (1998), 17:243-252.
Cezary Leonard Hebda, *Microbiological Hydroxylations of TricyclicSesuiterpenoid System (Hydroxylation, Sesquiterpenoid)*, Ph.D. Dissertation, (1991), Wroclaw Technical University, Wrocklaw, Poland.
M.S. Karawya et al., *Essential Oil of Egyptian Guajava Leaves*, Egypt J. Pharm. Sci., (1999), vol. 40, No. 2, 209-217.
Paul Thomas Kurtulik, *Isolation and Characterization of Novel Antimicrobial Agents and Other Components from Lophira Lanceolata*, Ph.D. Dissertation, (1982), Rutgers University The State of U. of New Jersey (New Brunswick).
N. Lall et al., *In Vitro Inhibition of Drug-Resistant and Drug Sensitive Strains of Mycobacterium tuberculosis by Enthnobotanically Selected South African Plants*, J. Ethnopharmacology, (1999), 66:347-354.
Sandra M. Newton et al., *A Review of Antimycobacterial Natural Products*, Phytotherapy Research, (2000), 14:303-322, John Wiley & Sons, Ltd.
Babajide Olanrewaju Oguntimein, *Biolgically Active Constituents of Uvaria Species*, Ph.D. Dissertation, (1981), The University of Mississippi.
Nalin Rastogi et al., *Antimycobacterial Activity of Chemically Defined Natural Substances from the Caribbean Flora in Guaderloupe*, FEMS Immuno. Med. Microbiol., (1998), 20:267-273.
Steven Lynn Robbs, *A Search for Biologically Active Phytochemicals from Endemic Plants of the Southwestern United States*, Ph.D. Dissertation, (1997), The Louisiana State University and Agricultural and Mechanical College.
F. M. Soliman et al., *Analysis and Biological Activity of the Essential Oil of Rosmarinus officinalis L. from Egypt*, Flavour and Fragrance Journal, (1994), 9:29-33, John Wiley & Sons, Ltd.
K. C. Wong et al., *Steam Volatile Constituents of the Aerial Parts of Paederia*, Flavour and Fragrance Journal, (1994), 9:25-28, John Wiley & Sons, Ltd.
Amelio Mauro et al: Database Biosis [Online], Biosciences Information Service, Philadelphia, PA US; Apr. 1988 "Separation of stigmasta-3,5-diene, squalene isomers, and wax esters from olive oils by single high-performance liquid chromatography run."
Jose C. Del Rio et al., *Analysis Of Pitch Deposits Produced In Kraft Pulp Mills Using A Totally Chlorine Free Bleaching Sequence*, Journal of Chromatography A, 874 (2000) 235-245.
W. Moreda et al., *Gas And Liquid Chromatography Of Hydrocarbons In Edible Vegetable Oils*, Journal of Chromatography A, 936 (2001) 159-171.

(Continued)

*Primary Examiner*—Patricia Leith
(74) *Attorney, Agent, or Firm*—Michael David, Esq.; Whiteford, Taylor & Preston, LLP

(57) ABSTRACT

The invention provides a pharmaceutical composition which comprises a pharmaceutical carrier and at least one compound selected from the group consisting of cobaltocene-octamethyl, stigmastan- 3,5 -diene, galoxolide, benzyl salicylate, eucalyptol, and α-pinene. Also provided is a method of preparing a composition having antimicrobial activity comprising extracting a plant material in an organic solvent, contacting the extracted material to a chromatographic column, and eluting from the chromatographic column with a mobile polar phase to obtain a composition. The plant material is from *Mammea Americana, Marchantaceae polymorpha,* or *Callistemon citrinus*. Also provided is a method of inhibiting the growth of a mycobacterium, comprising administering a composition comprising a carrier and at least one compound selected from among cobaltocene-octamethyl, stigmastan, 3,5 -diene, friedelin, galoxolide, benzyl salicylate, eucalyptol, and α-pinene.

9 Claims, 3 Drawing Sheets

OTHER PUBLICATIONS

Morris J. A. et al: "*Antimicrobial Activity of Aroma Chemicals and Essential Oils*", Journal of the American Oil Chemists' Society, American Oil Chemists' Society, Campaign, US, May 1, 1979 (Jun. 1, 1979), pp. 595-603.

Pattnaik S. et al: "*Antibacterial and Antifungal Activity of Aromatic Constittuents of Essential Oils*" Microbios, Cambridge, GB, vol. 358, No. 89, 1997, pp. 39-46.

Deans S. G. et al: "*Antimicrobial Activity of French Tarragon (Artemisia dracunculus Linn.) Essential IOL and its Constituents During Ontogeny*" Journal of Horticulture Scienes, Headley Bros. Ltd., Invicta Press, Ashford, GB, vol. 63, No. 3, 1988, pp. 503-508.

Kamory, E. et al: "*Isolation and antibacterial activity of marchantin A, a cyclic bis(bibenzyl) constituent of Hungarian Marchantia polymorpha.*", Planta Medica vol. 61, No. 4, Aug. 1995, pp. 387-388.

Grange J. M. et al: "*Detection of antituberculous activity in plant extracts.*" The Journal Of Applied Bacteriology. England Jun. 1990, vol. 68, No. 6, Jun. 1990 pp. 587-591.

Yoshimoto Ohta et al., Prelunularic Acid in Liverworts, Phytochemistry, vol. 23, No. 8, pp. 1607-1609, 1984.

Yih-Dih Cheng et al., Component Analysis of Black Ant (*Polyrhachis lamellidens*) Extracts from Supercritical Fluid Extraction, Journal of Food and Drug Analysis, vol. 9, No. 2, 2001, pp. 72-78.

Frame, A., et al., "Plants from Puerto Rico with anti-Mycobacterium tuberculosis properties." Puerto Rico Health Sciences Journal, Puerto Rico, Sep. 1998, vol. 17, No. 3, pp. 243-252.

Amory, E., et al., "Isolation and Antibacterial Activity of Marchantin A, a Cyclic Bis(bibenzyl) Constituent of Hungarian Marchantia polymorpha." Planta Medica, Germany, Aug. 1995, vol. 61, No. 4, pp. 387-388.

Eicher, H., et al., "Determination of the electronic structure, the spin density distribution, and approach to the geometric structure of substituted cobaltocenes from NMR spectroscopy in solution." Chemical Physics, Netherlands, Dec. 15, 1988, vol. 128, Issues 2-3, pp. 297-309.

Kohler, F., et al., "NMR-Spectroscopy on Paramagnetic Complexes, XXVII. Paramagnetic 1,1',2,2',3,3', 4,4'- octamethylmetalocenes." Zeitschriff fuer Naturforschung, Germany, Teil B: Anorganische Chemie, Organische Chemie, 37b(2), 1982, pp. 144-150.

* cited by examiner

ANTI-BACTERIAL PLANT COMPOSITIONS

CROSS REFERENCE TO RELATED PATENT APPLICATIONS

This application is a continuation of PCT/US 01/50502, which was filed on Dec. 28, 2001.

FIELD OF THE INVENTION

This invention pertains to isolation and use of extracted and purified plant compounds, which have anti-microbial and anti-mycobacterial activity.

BACKGROUND OF THE INVENTION

The Mycobacterium genus includes numerous bacterial species that cause disease in man, other mammals, and birds. For example, M. tuberculosis is the causative agent of the most common infectious disease in the world today, tuberculosis. The World Health Organization (WHO) reported that 1.7 billion people (or approximately one-third of the world's population) are or have been infected at one point in their lives by M. tuberculosis. Kochi, A. Tubercle 72:1-6 (1991). It is estimated that 10 to 15 million people in the U.S. have latent infections. Morbidity and Mortality Weekly Report 39(RR-8):9-12 (1990). It is calculated that 8 million new clinical tuberculosis cases occur worldwide per year and approximately 3 million people die annually. Morbidity and Mortality Weekly Report 42 (49):961-964 (1993).

Mycobacteria of the MAC complex (primarily M. avium and M. intracellulare) are opportunistic pathogens in AIDS patients. Approximately 43% of AIDS patients at advanced stages of the disease suffer MAC infections. Nightingale et al., J. Infect. Dis. 165:1082-1085 (1992). In addition to AIDS related infections, M. paratuberculosis, a subspecies of M. avium is thought to be associated with Crohn's disease, an inflammatory disease of the bowel. Chiodini, R. J. Clin. Micro. Rev. 2:90-117 (1989).

Additional mycobacteria which are considered human pathogens, include M. leprae, M. kansasii, M. marinum, M. fortuitum complex, M. bovis, M. scrofulaceu, and M. ulcerans. Baron, S., editor, MEDICAL MICROBIOLOGY, Second Edition, pages 562-564 Addison-Wesley Pub. Co., Menlo Park, Calif. (1996); Wayne, L. G. et al., Clin. Micro. Rev. 5:1-25 (1992). There are an estimated 5.5 million cases of M. leprae infections worldwide. Nordeen, S. K. et al., Int. J. Lepr. 63:282-287 (1993).

M. paratuberculosis also causes bowel inflammations in ruminants, more commonly known as Johne's disease. Thoen, C. O. et al., Rev. Infect. Dis. 3:960-972 (1981). Cattle that test positive for M. paratuberculosi are culled and destroyed. The incidence among herds nationwide typically ranges between 3% and 18%. Merkal, R. S. et al., J. Am. Vet. Med. Assoc. 190:676-680 (1987). The financial impact of this disease on the dairy industry exceeds $1.5 billion annually. Whitlock, R. PROCEED. OF THE THIRD INTERNAT. COLLOQ. PARATUBERCUL., pp.514-522 (1991). M. bovis is another mycobacteria of importance in veterinary medicine. M. fortuitum is a soil bacterium that has been isolated from lesions in animals and humans. M. avium causes a disease in chicken, a serious concern to the poultry industry. M. marinum infects cold-blooded animals and fish; it has also been isolated from superficial granulomas on the extremities of humans.

Extracts from several hundred plant species have been tested to date for anti-cancerous, anti-microbial, anti-bacterial and, sometimes, anti-mycobacterial activity. The total extract or, sometimes the oil from plant tissue ranging from leaf, stem, and root, were shown to have various levels of activity. In most cases, the chemical composition of the material has not been described. For a review, see Newton et al., Phytother. Res., 14:303-322 (2000). See also Soliman et al., Flavour and Fragrance Journal, 9(1): 29-33 (1994); Hebda, Dissertation Abstracts International, 53(4-C): 737 (1991); Robbs, Dissertation Abstracts International, 58(6-B): 3009 (1997); Kurtulik, Dissertation Abstracts International, 43(4-B): 1050 (1982); Oguntimein, Dissertation Abstracts International, 42(02-B): 577 (1981); Frame et al., P. R. Health Sci. J., 17: 243-252 (1998); Lall et al., J Ethnopharmacol, 66: 347-354 (1999); and Rastogi et al., FEMS Immuno. Med. Microbiol. 20: 267-273 (1998). Thus, a need for identification of pure and effective anti-mycobacterial chemical compounds remains. Generally, the results were disappointing in regard to identification of lead plant extracts with anti-mycobacterial activity. See Newton (2000) supra. However, see Rejab et al., Phytotherapy Research, 14: 303-322 (2000), George et al., Phytotherapy Research, 14: 303-322 (2000), and Lall et al, supra.

The lipoidal nature of the mycobacterial cell wall appears to contribute to survival of mycobacteria by rendering them resistant to drying and acid or alkaline conditions. For example, mycobacteria survive acid or alkaline conditions and heat sterilization of limited duration. Mycobacterium has proved to be a tough, difficult to control bacteria. New infective mycobacteria can be retrieved after several months from old cultures or contaminated surfaces. New agents that can control mycobacterial contamination are needed.

A new fear of tuberculosis has resulted from reports about outbreaks with multidrug resistant strains of M. tuberculosis (MTB) in the United States. These strains are resistant to at least the most important antituberculotic drugs, isoniacid and rifampicin. The frequency of multidrug-resistant tuberculosis in the USA is reported to be 3-7% and about 19% in New York. Thus there is an urgent need for new and effective antimycobacterial agents to replace or add to those currently in use.

SUMMARY OF THE INVENTION

In one aspect, the invention provides a pharmaceutical composition comprising a pharmaceutical carrier and at least one compound selected from the group consisting of cobaltocene-octamethyl and stigmastan-3,5,-diene. In accordance with a preferred embodiment, the composition comprises cobaltocene-octamethyl, stigmastan-3,5,-diene, and friedelin. In accordance with another preferred embodiment, the composition further comprises at least one compound selected from the group consisting of α-caryophylene, β-caryophylene, caryophylene oxide, cyclododecane, acetic acid, and a terpene.

Also provided is a pharmaceutical composition comprising a pharmaceutical carrier and at least one compound selected from the group consisting of galoxolide, benzyl salicylate, eucalyptol, and α-pinene. In accordance with a preferred embodiment, the pharmaceutical composition comprises galoxolide, benzyl salicylate, eucalyptol, and α-pinene. In accordance with another preferred embodiment, the pharmaceutical composition further comprises at least one compound selected from the group consisting of 3-cyclohexane-1-methanol, camphene, 1,4-cycloprop-azulene, and phytol. The pharmaceutical composition includes these components in isolated or purified form In accordance with another aspect of the invention, it is provided a method of preparing a composition having antimicrobial activity comprising extracting a plant material in an organic solvent, contacting the extracted material with a chromatographic separation system, and eluting from the chromatographic separation system with a mobile polar phase to obtain a composition. The plant material is obtained from *Mammea Americana, Marchantia polymorpha*, or *Callistemon citrinus*, and the composition has antimicrobial activity.

In accordance with yet another aspect of the invention, it is provided a method of inhibiting the growth of a mycobacterium, comprising administering a composition comprising a carrier and at least one compound selected from among cobaltocene-octamethyl, stigmastan, 3,5-diene, galoxolide, benzyl salicylate, eucalyptol, and α-pinene. The mycobacteria is *M. avium, M. bovis, M. intracellulare, M. kansaii, M. leprae, M. marinum, M. phlei, M. scrofulaceum, M. smegmatis, M. fortuitum, M. tuberculosis*, or *M. ulcerans*.

DETAILED DESCRIPTION OF THE INVENTION

Figure 1:
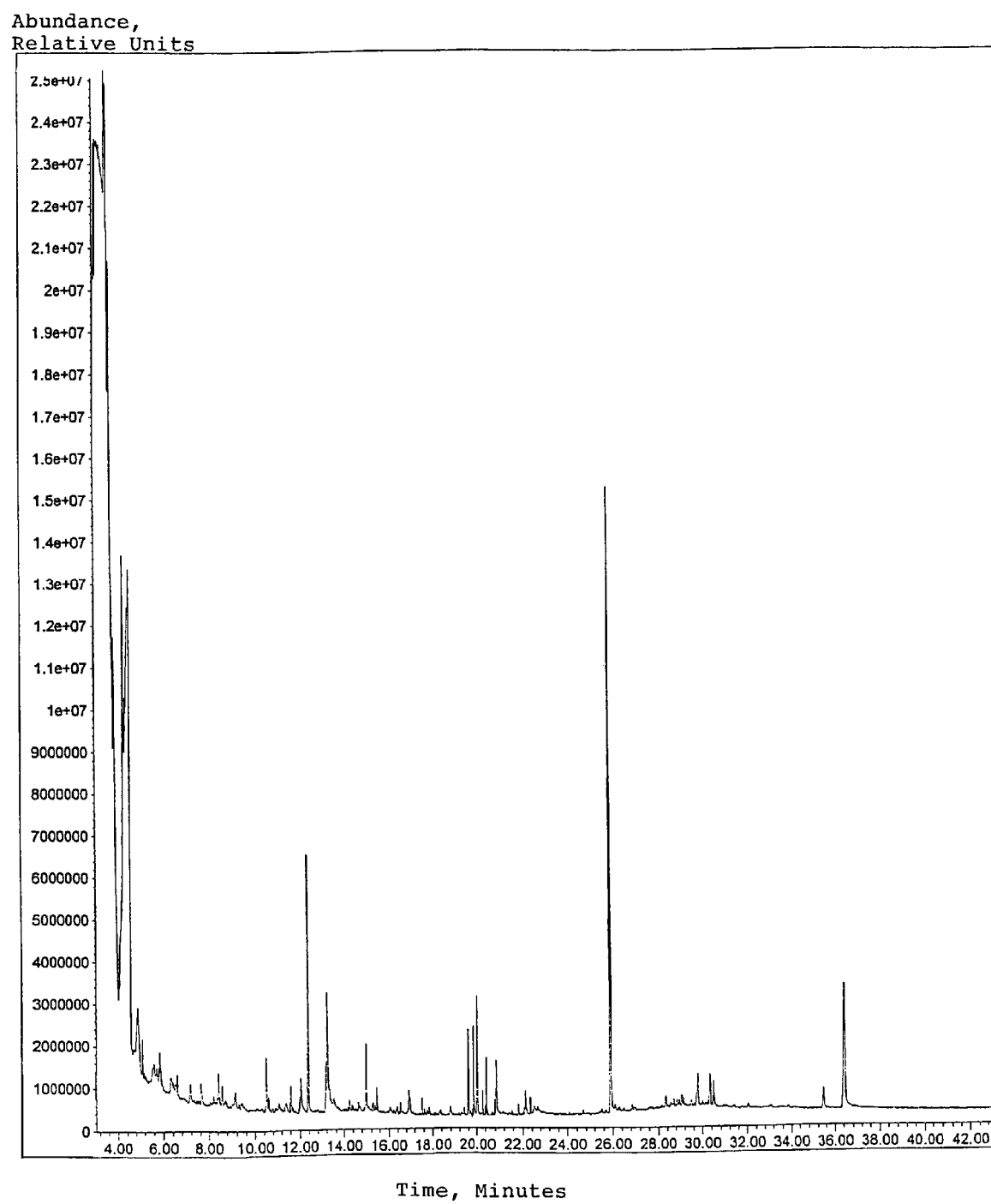
FIG. 1 is a Gas Chromatography/Mass Spectroscopy (GC/MS) analysis of an active fraction of *Mammea Americana*. The material was prepared by combination of 4 HPLC runs, concentrated to 1 drop to which about 0.3 ml methanol was added. 10 .mu.l were analyzed on GC/MS. The peaks were identified. The peak at 13 minutes is cobaltocene, 1,1',2,2',3, 3',4,4'-octamethyl, the peak just past 30 minutes is stigmastan-3,5-dien, and the peak just past minute 36 is friedelin.

The invention was made possible by the identification and isolation of purified plant fractions and compounds which were shown to have antimicrobial activities. In accordance with one aspect of the invention, there is provided a method of preparing a composition having antimicrobial activity. The method comprises extracting a plant material in an organic solvent, contacting the extracted material to a chromatography separation system, and eluting the extract from the chromatography separation system with a mobile polar phase to obtain a composition which has antimicrobial activity. The plant material is from *Mammea Americana, Marchantia polymorpha*, or *Callistemon citrinus*.

Any part of the plant can be subjected to the extraction procedure. For example, seed, stem, leaf, flower, or plant sap may be the plant material which is extracted with an organic solvent. In accordance to a preferred embodiment, the plant material is leaf The organic solvent comprises, preferably, a polar solvent. The organic solvent can comprise one solvent or it can be a mixture of solvents. Buffers or salts may be added in a manner which is well known to an artisan skilled in the art. In accordance with one embodiment, the solvent is hydrogen bonding. The hydrogen bonding solvent can be, for example, a hydroxy, a carboxy, or an amine containing solvent. Preferably, the solvent includes an alcohol. In accordance with a more preferred embodiment the solvent is ethanol, and, in accordance with another preferred embodiment, the solvent is methylene chloride. The actual extraction procedures are well known in the art. For example, either shaking in a solvent or a dripping of the solvent over the plant tissue can be used.

The chromatographic separation system can be of any suitable type. Any separation system that allows use of a polar mobile phase can be used in the invention. Preferably, the chromatographic separation system would have sufficient capacity for separation of as much plant material as possible. For example, the separation may be thin layer chromatography (TLC), a sephadex or sepharose column, DEAE-cellulose, or a high pressure liquid chromatography (HPLC) system. In a preferred embodiment, the chromatographic separation is an HPLC system. In accordance with an embodiment, an amide based column is used.

Any mobile polar phase can be used to obtain an isolated and pure compound or set of compounds. Generally, a more polar mobile phase is preferred over a less polar mobile phase. Preferably, the solvent can comprise a polar solvent and a salt, such as NaCl, or phosphoric acid. The mobile polar phase can comprise a hydrogen bonding solvent. The hydrogen bonding solvent would, for example, be a hydroxy, carboxy, or an amine based solvent. In one embodiment, the solvent of the mobile phase contains an alcohol. In accordance to a preferred embodiment the solvent of the mobile phase is methanol, and, in accordance with a more preferred embodiment, the polar mobile phase comprises a mixture of methanol and phosphoric acid. In accordance with a preferred embodiment the methanol-phosphoric acid mobile phase comprises from 1 mM to at least about 20 mM phosphoric acid, preferably about 10 mM. The mobile polar phase can be isocratic, i.e. one concentration, or it can be a gradient from 1% to 99%.

Fractions are collected and analyzed by any suitable analytical techniques, for example by ultra-violet visualization of the material eluted as a function of time, or by the use of TLC. A fraction which has anti-microbial activity is next identified. Once a set of conditions are known, then it can become the standard for collection of active fractions or compounds, e.g., the retention time on a column under a set of conditions is a guidance for further isolation of purified active fractions or compounds from the same plant.

The fractions isolated, as well as the compounds isolated and purified from these fractions are tested for antimicrobial activity. The fractions and compounds having antimicrobial activity are hereinafter sometimes referred to as being "active."

For example, an anti-microbial activity can be demonstrated by contacting the extracted material, the purified and isolated fraction, or an isolated and purified compound, or a composition thereof, to an microbe and determining the susceptibility of the microbe. The microbe can be any microbe, for example, a bacterium, a fungus, or a protozoa. Preferably, the microbe is a bacterium. More preferably, the bacterium is from the Escherichia genus or the Mycobacterium genus. More preferably yet, the Mycobacterium is a pathogenic bacteria, pathogenic to man, animals or birds. Most preferably, the bacterium is *M. tuberculosis*.

An artisan skilled in the art will know how to determine susceptibility by standard assays, well known in the art. The artisan skilled in the art will know how to conduct the assay including appropriate controls, negative and positive, to ensure the results of the assay are meaningful. The assay chosen might depend on the organism tested for susceptibility. For examples of mycobacterial assays (which can be easily converted by a skilled artisan for testing other microbes) see Newton et al, supra (2000). For example, most commonly, the test methods employed are the disc diffusion and the broth dilution methods. In the disc diffusion method, paper discs impregnated with the extract under test are placed on a semi-solid (agar based) medium which has been inoculated with mycobacteria. After incubation, zones of inhibition of bacterial growth around the discs are measured. In the broth dilution method, the minimum concentration required to inhibit bacterial growth (minimum inhibitory concentration, MIC) is determined using a series of tubes containing serial dilutions of the extract in inoculated broth.

For high-throughput screening, rapid methods which can be automated are known; these have been reviewed by Gordon et al., *Phytotherapy Research* 14:303-322 (1996). For example, measuring the evolution of $^{14}CO_2$ from *M. tuberculosis* cultured in medium containing $^{14}C$-palmitic acid formed the basis for the BACTE system (Becton-Dickinson, Oxford, UK). The BACTE system is used for the susceptibility testing of clinical isolates and can provide results in a few days compared with 3-4 weeks for conventional methods. Chung et al., *Phytotherapy Research* 14:303-322 (1995) developed an assay based on measuring the uptake of radio-labelled uracil into *M. aurum*.

Assays were developed in which mycobacterial viability is determined using either bacterial or firefly luciferase. The bacterial enzyme uses reduced flavin (produced by viable mycobacteria) to oxidize an added aldehyde substrate (decanal) which is accompanied by the production of light at 490 nm. Firefly luciferase depends upon ATP generated by the mycobacteria to decarboxylate luciferin, resulting in the production of light at 562 nm. Light production may be measured easily using a luminometer in high-throughput systems. Several species of mycobacteria, including *M. tuberculosis*, have been genetically modified by inserting the genes for the production of bacterial luciferase; only viable bacilli emit light when decanal is added and there is no requirement for growth so that susceptibility testing may be carried out rapidly. Similarly, the gene for firefly luciferase has been incorporated into a number of mycobacteria species including *M. Aurum*. Id.

Colorimetric methods are suitable for use in microtitre plates and the results may be easily obtained using a spectrophotometer. Gomez-Florex et al. *J. Clin. Microbiol.* 33: 1842-1846 (1995) reported as assay for testing against the *M. avium* complex which depends on the ability of viable bacteria to reduce dimethylthiazoldiphenyltetrazolium to formazan. Another similar method utilizes the redox dye Alamar blue which changes color from blue to pink in the presence of viable *M. tuberculosis* (Yajko et al., *J. Clin. Microbiol.* 33:2324-2327 (1995).

It may be valuable to evaluate the ability of plant compounds to inhibit *M. tuberculosis* within cultured human macrophages. This may be carried out by the methodology of Crowle and May, *Antimicrob. Agents Chemother.* 34:2217-2222 (1990).

An artisan skilled in the art will appreciate that "an isolated and pure" fraction, compound or compounds are always accompanied by some other material. Here, "an isolated and pure" fraction, compound or compounds refers to a fraction, compound or compounds, which is at least 100, preferably 150, 200, 300, 400, 500, 600, 700, 800, 1000, 2000, 3000, 4000, 5000, 6000, 7000, 8000, 9000, 10000, or more than 10000 fold more abundant by weight, or volume, or weight/volume to its weight, or volume, or weight/volume in the starting material (here the plant tissue). Alternatively, a skilled artisan may express "isolated and purified' in terms of purity. If so, the active fraction, compound, or compounds of the invention are at least 70%, preferably, 80%, 85%, 90%, 91%, 92%, 93%, 94%, 95%, 96%, 97%, 98%, 99%, 99.5%, or more pure, relative to the starting material (herein, the plant tissue).

Initially, *Mammea Americana*, *Marchanti polymorpha*, and *Callistemon citrinus* tissue, separately, was extracted with ethanol and the extract was shown to have activity against *E. coli* and *M. smegmatis*. Analysis by Gas Chromatagraphy/Mass Spectroscopy (GC/MS) and comparison of the resultant profile to the profile of known compounds revealed a large set of compounds in the extract. For example, known compounds can be identified by this method by comparing the profile with known profiles in databases. One preferable such database is a library of molecular cracking patterns, referred to as the 129K NIST Mass Spectroscopy Library, available from the National Institute of Standards and Technology, Washington, D.C. When the same set of extraction and analysis (anti-microbial activity and GC/MS) was performed on additional plant material, but the extraction solvent was methylene chloride, the number of compounds identified in the anti-microbially active extract was smaller (each thus more pure). Most interestingly, despite the fact that the active compound was present in both extracts, there was little overlap between the compounds in the ethanol and the methylene chloride extracts (and for some plants no overlap). See Tables 2-4. This provided an indication that only one or very few compounds were responsible for the anti-microbial activity in each plant, and if more than one compound, the active compounds had very similar solubility properties, because they co purified in two different extraction systems.

Methylene chlorine extracts from *Mammea Americana*, *Marchantaceae polymorpha*, or *Callistemon citrinus* were separated on a HPLC system. Active fractions were identified. Active compounds were next identified. The compounds from *Mammea Americana* include cobaltocene-octamethyl, stigmastan-3,5-diene, and friedelin. In addition, consideration of the chemical properties of the compounds in the extract before fractionation indicates that one or more of α-caryophylene, β-caryophylene, caryophylene oxide, cyclododecane, acetic acid, and a terpene may also be present in trace (i.e. undetectable by GC/MS under the conditions described herein) quantities.

The compounds from *Marchantaceae polymorpha* include acetic acid, cobaltocene-octamethyl, and β-myrceane. In addition, consideration of the chemical properties of the compounds in the extract before fractionation indicates that hexadecanoic acid may also be present in trace quantities.

The compounds from *Callistemon citrinus* include galoxilide, benzyl salicylate, eucalyptol, and α-pinene. In addition, consideration of the chemical properties of the compounds in the extract before fractionation indicates that one or more of 3-cyclohexane-1-methanol, camphene, 1,4-cycloprop-azulene, or phytol may also be present in trace quantities.

In accordance with another aspect of the invention, a pharmaceutical composition comprising a pharmaceutical carrier and at least one compound selected from the group consisting of cobaltocene-octamethyl or stigmastan-3,5,-diene is provided. In accordance with a preferred embodiment, the pharmaceutical composition comprises cobaltocene-octamethyl, stigmastan-3,5-diene, and friedelin. The pharmaceutical composition may further comprise at least one compound selected from the group consisting of α-caryophylene, β-caryophylene, caryophylene oxide, friedelin, cyclododecane, acetic acid, and a terpene.

In accordance with another aspect of the invention, a pharmaceutical composition comprising a pharmaceutical carrier and at least one compound selected from the group consisting of galoxolide, benzyl salicylate, eucalyptol, and α-pinene is provided. In accordance with a preferred embodiment, the composition comprises galoxolide, benzyl salicylate, eucalyptol, and α-pinene. The pharmaceutical composition may further comprise at least one compound selected from the group consisting of 3-cyclohexane-1-methanol, camphene, 1,4-cycloprop-azulene, and phytol.

The pharmaceutical composition may include pharmaceutically acceptable salts and carriers. Examples of pharmaceutically acceptable salts include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, and arylsulfonic acids. An example of arylsulphonic acid is p-toluenesulphonic acid. For example, a carboxyl group of the compound or fraction may be converted to salts known to those of average skill in the art, for example, a salt of an alkali metal (e.g., sodium or potassium), alkaline earth metal (e.g., calcium), or ammonium of salt. The present invention further provides a pharmaceutical composition comprising a compound (or compound or fraction) described above and a pharmaceutically acceptable carrier.

Generally, the compounds or fractions of the present invention as described above will be administered in a pharmaceutical composition to an individual infected or suspected to be infected by a pathogenic microbe, for example a mycobacterium. Those undergoing or about to undergo chemotherapy can be treated with the compounds or fractions separately or in conjunction with other treatments, as appropriate. In therapeutic applications, compositions are administered to a patient in an amount sufficient to elicit a limitation of the growth of the pathogenic microbe. An amount adequate to accomplish this is defined as a "therapeutically effective dose." Amounts effective for a therapeutic or prophylactic use will depend on, e.g., the stage and severity of the disease being treated, the age, weight, and general state of health of the patient, and the judgment of the prescribing physician. The size of the dose will also be determined by the compound or fraction selected, method of administration, timing and frequency of administration as well as the existence, nature, and extent of any adverse side-effects that might accompany the administration of a particular compound or fraction and the desired physiological effect. It will be appreciated by one of skill in the art that various disease states may require prolonged treatment involving multiple administrations, perhaps using a series of different compounds or fractions of the invention in each or various rounds of administration.

Suitable doses and dosage regimens can be determined by conventional range-finding techniques known to those of ordinary skill in the art. Generally, treatment is initiated with smaller dosages that are less than the optimum dose of the compound or fraction. Thereafter, the dosage is increased by small increments until the optimum effect under the circumstances is reached. The present inventive method may involve the administration of about 0.1 μg to about 50 mg of one or more of the compounds or fractions per kg body weight of the individual. For a 70 kg patient, dosages of from about 10 μg to about 200 mg of the compound or fraction would be more commonly used, depending on a patient's physiological response, as determined by measuring pathogen growth limitation or inhibition.

It must be kept in mind that the compounds or fractions and compositions of the present invention may be employed in many disease states including life-threatening or potentially life-threatening situations. It is possible and may be felt desirable by the treating physician to administer some or substantial excess of the compound or fraction. Single or multiple administrations of the compounds or fractions can be carried out with dose levels and pattern being selected by the treating physician.

The pharmaceutical compositions for therapeutic treatment are intended for parenteral, topical, oral or local administration and generally comprise a pharmaceutically acceptable carrier and an amount of the active ingredient sufficient to inhibit growth of the pathogenic microbe. The carrier may be any of those conventionally used and is limited only by chemico-physical considerations, such as solubility and lack of reactivity with the compound or fraction, and by the route of administration.

The pharmaceutically acceptable carrier (or excipient) is preferably one that is chemically inert to the compound or fraction or the active compound and one that has no detrimental side effects or toxicity under the conditions of use. Such pharmaceutically acceptable carriers preferably include saline (e.g., 0.9% saline), Cremophor EL (which is a derivative of castor oil and ethylene oxide available from Sigma Chemical Co., St. Louis, Mo.) (e.g., 5% Cremophor EL/5% ethanol/90% saline, 10% Cremophor EL/90% saline, or 50% Cremophor EL/50% ethanol), propylene glycol (e.g., 40% propylene glycol/10% ethanol/50% water), polyethylene glycol (e.g., 40% PEG400/60% saline), and alcohol (e.g., 40% t-butanol/60% water). A preferred pharmaceutical carrier is polyethylene glycol, such as PEG 400, and particularly a composition comprising 40% PEG 400 and 60% water or saline. The choice of carrier will be determined in part by the particular compound or fraction chosen, as well as by the particular method used to administer the composition. Accordingly, there are a wide variety of suitable formulations of the pharmaceutical composition of the present invention.

The following formulations for oral, aerosol, parenteral, subcutaneous, intravenous, intraarterial, intramuscular, interperitoneal, rectal, and vaginal administration are merely exemplary and are in no way limiting. The pharmaceutical compositions can be administered parenterally, e.g., intravenously, intraarterially, subcutaneously, intradermally, or intramuscularly. Thus, the invention provides compositions for parenteral administration that comprise a solution of the compound or fraction dissolved or suspended in an acceptable carrier suitable for parenteral administration, including aqueous and non-aqueous, isotonic sterile injection solutions.

Overall, the requirements for effective pharmaceutical carriers for parenteral compositions are well known to those of ordinary skill in the art. See *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986). Such compositions include solutions containing anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound or fraction may be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils useful in parenteral formulations include petroleum, animal, vegetable, and synthetic oils. Specific examples of oils useful in such formulations include peanut, soybean, sesame, cottonseed, corn, olive, petrolatum, and mineral oil. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof The parenteral formulations typically will contain from about 0.5% or less to about 25% or more by weight of the active ingredient or compound or fraction in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets.

Topical formulations, including those that are useful for transdermal drug release, are well-known to those of skill in the art and are suitable in the context of the present invention for application to skin.

Formulations suitable for oral administration can consist of (a) liquid solutions, such as an effective amount of the compound or fraction dissolved in diluents, such as water, saline, or orange juice; (b) capsules, sachets, tablets, lozenges, and troches, each containing a predetermined amount of the compound or fraction, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising a compound or fraction in an inert base, such as gelatin and glycerin, or sucrose and acacia, emulsions, gels, and the like containing, in addition to the compound or fraction, such excipients as are known in the art.

The compounds or fractions of the present invention, alone or in combination with other suitable components, can be made into aerosol formulations to be administered via inhalation. The compounds or fractions are preferably supplied in finely divided form along with a surfactant and propellant. Typical percentages of active compound or fraction may be about 0.01% to about 20% by weight, preferably about 1% to about 10% by weight. The surfactant must, of course, be nontoxic, and preferably soluble in the propellant. Representative of such surfactants are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute from about 0.1% to about 20% by weight of the composition, preferably from about 0.25% to about 5%. The balance of the composition is ordinarily propellant. A carrier can also be included as desired, e.g., lecithin for intranasal delivery. These aerosol formulations can be placed into acceptable pressurized propellants, such as dichlorodifluoromethane, propane, nitrogen, and the like. They also may be formulated as pharmaceuticals for non-pressured preparations, such as in a nebulizer or an atomizer. Such spray formulations may be used to spray mucosa.

Additionally; the compounds or fractions may be made into suppositories by mixing with a variety of bases, such as emulsifying bases or water-soluble bases. Formulations suitable for vaginal administration may be presented as pessaries, tampons, creams, gels, pastes, foams, or spray formulas containing, in addition to the active ingredient, such carriers as are known in the art to be appropriate.

The concentration of the compounds or fractions of the present invention in the pharmaceutical formulations may vary, e.g., from less than about 1%, usually at or at least about 10%, to as much as 20% to 50% or more by weight, and may be selected primarily by fluid volumes, and viscosities, in accordance with the particular mode of administration selected.

Thus, a typical pharmaceutical composition for intravenous infusion could be made up to contain 250 ml of sterile Ringer's solution, and 100 mg of the compound or fraction. Actual methods for preparing parenterally administrable compounds or fractions will be known or apparent to those skilled in the art and are described in more detail in, for example, *Remington's Pharmaceutical Science* (17th ed., Mack Publishing Company, Easton, Pa., 1985).

It will be appreciated by one of ordinary skill in the art that, in addition to the aforedescribed pharmaceutical compositions, the compounds or fractions of the present inventive method may be formulated as inclusion complexes, such as cyclodextrin inclusion complexes, or liposomes. Liposomes may serve to target the compounds or fractions to a particular tissue, such as lymphoid tissue or cancerous hepatic cells.

Liposomes can also be used to increase the half-life of the compound or fraction. Many methods are available for preparing liposomes, as described in, for example, Szoka et al., *Ann. Rev. Biophys. Bioeng.*, 9, 467 (1980), and U.S. Pat. Nos. 4,235,871, 4,501,728, 4,837,028, and 5,019,369.

In accordance with another aspect of the invention, a method of inhibiting the growth of a mycobacterium, comprising administering a composition comprising a carrier and at least one compound selected from among cobaltoceneoctomet, stigmastan, 3,5,-diene, galoxolide, benzyl salicylate, eucalyptol, and α-pinene is provided. The composition is appropriately formulated for storage and is destined for use as a cleaning agent. Accordingly, it may further comprise cleaning agents which would not interfere with the chemical activity of the above listed chemical agents. The formulation of such a cleaning solution and inclusion of general cleaning agents can easily be done by a skilled artisan, given theoretical chemistry considerations, and the stability and effectiveness of the solution can be easily tested by the skilled artisan. The testing would include a bio-assay such as the anti-microbial assays. The preparation and composition of such a cleaning solution is also within the scope of the invention.

The cleaning solution is active against at least mycobacteria or *E. coli*. Following is a listing of mycobacteria and sub groupings which are inhibited by the active compounds, the active fractions, and the methods of the invention. Mycobacterium group or complex or Mycobacterium species, and most preferred, a Mycobacterium complex such as *M. tuberculosis* (MTB) complex, *M. avium* (MAC) complex, MAIS complex and *M. fortuitum* complex, are inhibited, as well as fast growing and slow growing (i.e. less than 60 minutes average generation time in standard laboratory conditions) mycobacteria including specified and unspecified photochromogens, nonphotochromogens, scotochromogens, and especially *M. africanum, M. asiaticum, M. avium, M. bovis, M. bovis* (BCG), *M. butyricum, M. chelonae, M. duvalii, M. flavescens, M. fortuitum, M. gastri, M. gordonae, M. haemophilum, M. intracellulare, M. kansasii, M. leprae, M. lepraemurium, M. linda, M. lufu, M. marinum, M. malmoense, M. microti, M. mucoscum, M. nonchromogenicum, M. paratuberculosis, M. peregrinur, M. phlei, M. rhodochrous, M. scrofulaceum, M. shimoidei, M. simiae, M. smegmatis, M. szulgai, M. terrae, M. thermoresistable, M. triviale, M. tuberculosis, M. ulcerans, M. vaccae, M. xenopi*, and serovats thereof *M. kansasii, M. marinum, M. simiae* and *M. asiaticum* are examples of photochromogens. *M. scrofulaceum, M. szulgai, M. xenopi, M. gordonae* and *M. flavescens* are examples of scotochromogens. *M. avium, M. intracellulare, M. gastri, M malmoense, M. terrae* and *M. triviale* are all examples of nonphotochromogens. *M. africanum, M. avium, M. bovis, M. haemophilum, M. intracellulare, M. kansasii, M. malmoense, M. marinum, M. microti, M. paratuberculosis, M. scrofulaceum, M. simiae, M. szulgai, M. tuberculosis*, and *M. xenopi* are all examples of slow-growing (requiring more than seven days) mycobacterial species. *M. chelonei, M. flavescens, M. fortuitum, M gordonae, M. leprae, M. phlei, M. smegmatis, M. terrae, M. ulcerans* are all examples of rapid-growing (requiring less than seven days for development of colonies on plates) mycobacterial species. *M. Tuberculosis, M. africanum, M. bovis, M. bovis* (BCG), and *M. microti* are members of the MTB complex. *M. avium* and *M. intracellulare* are the members of the MAC complex; there are at least three distinct serologic groups of *M. avium*, and more than 25 serovars of *M. intracellulare*.

The present invention, thus generally described, will be understood more readily by reference to the following examples, which are provided by way of illustration and are not intended to be limiting of the present invention.

EXAMPLE 1

This example demonstrates that *Mammea americana, Callistemon citrinus*, and *Merchantia polymorpha* ethanolic plant extracts have significant anti-mycobacterial activity but limited toxicity to shrimp and no detectable toxicity to mammals.

Approximately 3 pounds of plant leaves from 50 plant species were oven dried at 42° C., and ground in a blender. 30 gm. of the ground material were extracted in 300 ml of absolute ethanol (Spectrum Products laboratory, Garden, Calif.) by shaking at room temperature for 24-36 hrs. The liquid was then filtered on Whatman paper #4, then #2 (VRW Scientific Laboratory, Willard, Ohio) and evaporated at 40° C. on a Buchi/Beckman rotary evaporator (VRW Scientific Laboratory, Willard, Ohio). For testing, the material was resuspended in methanol, at the desired concentrations.

The activity of each extract was tested on *M. smegmatis* 607 (ATCC, Rockville, Md.). An agar-disk diffusion assay was performed, in parallel with assaying of extracts from other plants, and 10 µg streptomycin, water and methanol as controls. Bauer et al., *Amer. J. Clin. Path.*, 21:941-946 (1985). Multiple platings of each extract concentration and control were performed, and the zone of inhibition results tabulated and averaged. Among other plant extracts tested, the *Mammea americana, Callistemon citrinus*, and *Merchantia polymorpha* were found to be most active against *M. smegmatis*, showing a measurable and reproducible zone of inhibition when at least 25 µg, 25 µg, and 50 µg, respectively, of the resuspended extract was tested. Frame et al., supra (1998).

The activity of the extracts was tested also on *M. tuberculosis* 27294 (a streptomycin sensitive strain, ATCC, Rockville, Md.) by the BACTEC-460 method, wherein the inhibition of the growth is monitored in cultures grown in liquid cultures in the presence of the test substance or controls, by measurement of the $^{14}CO_2$ aspirated from the test vial. The results are presented as daily changes in growth rates or growth indexes (GI) of the tested culture relative to negative control cultures (water added to culture). Frame et al., supra (1998); and Siddiqi, *Bactec TB system: Product and Procedure Manual*, Becton Dickinson Diagnostic Instrument System, Towson, Md. (1989). Approximately 4.1 ml cultures were grown for up to 12 days and GI determined daily, starting on day 4. Again, additional plant extracts, and streptomycin (50 µg/ml final concentration), water, an untreated sample, and methanol (25 µl and 50 µl into a volume of 4.1 ml) were used as controls, and results of 3-6 repeats of each growth culture were averaged. The effects of the plant extracts were of a transitory nature, i.e., after numerous days, resistance to treatment reappeared. This suggests that *Mammea americana, Callistemon citrinus*, and *Merchantia polymorpha* extracts have bacteriostatic (as opposed to bacteriocidic) modes of action. By this assay, *M. tuberculosis* showed sensitivity to the *Mammea americana, Callistemon citrinus* and *Merchantia polymorpha* to 50 µg, 50 µg, and 100 µg extract, respectively. The sensitivity of *M. smegmatis* to *Mammea Americana* plant extract was approximately equivalent to sensitivity to streptomycin. See Table 1, where the results of 3-6 readings for each extract concentration are tabulated and where a negative control growth index indicator (ΔGI) was >30.

| Plant Extract from | Concentration (µg) | | | | |
|---|---|---|---|---|---|
| | 500µ | 250 µg | 100 µg | 50 µg | 25 µg |
| S. jambos | S | R | R | | |
| C. citrinus | S | S | S | R | R |
| M. charantia | S | R | R | R | R |
| M. polymorpha | S | S | S | R | R |
| M. indica | S | S | R | ND | ND |
| M. americana | S | S | S | S | R |

Positive control Streptomycin (50 µg/ml) resulting in a Δ G1 of −2.8
Methanol 0.1 ml resulting in a Δ G1 of −40
Methanol 0.2 ml resulting in a Δ G1 of 0.2.
S = susceptible
R = resistant Therefore, by two different assays systems, plant extracts from *Mammea Americana, Callistemon citrinus*, and *Merchantia polymorpha* were each shown to have significant activity against two different mycobacterial species.

EXAMPLE 2

Shows that there is no significant toxicity to mammals associated with plant extracts of *Mammea Americana, Callistemon citrinus*, or *Merchantia polymorpha*.

Groups of 7 CF-1 outbread mice (50 day-old males, average weight 30 gm) SASCO, Charles River Laboratories (Wilmington, Mass.) were tested by peritoneal administration to each group 500 µg of a plant extract resuspended in methanol, over a 15 day period, in daily injections of 100 µl. The plant extracts tested included *Mammea Americana, Callistemon citrinus*, and *Merchantia polymorpha*. Two groups of mice which received saline (100 µl) or saline and methanol mixture (50 µl each) were used as controls.

Mice remained under observation for a period of one month and the following parameters were measured on a daily basis: changes in activity, fecal consistency, hair condition, cutaneous lesions, eye changes, appetite (water and food intake), weight loss, temperature change and mortality.

In general, all six extracts derived from the plants included in the present work were well tolerated in the mice toxicity test. One mouse inoculated with *Marcanria polymorpha* extract died on day 13 due to sepsis caused by perforation of the intestine during innoculation. Another mouse injected with *Callistemon citrinus* died on day 15 after experiencing loss of appetite and weight for three consecutive days. The result from the necropsy performed one day after this mouse was found dead showed an undetermined cause of death.

It is concluded that mice exposed to about 16.7 µg plant extract per gm of body weight did not indicate toxic effects of the plant extracts.

EXAMPLE 3

This example demonstrates that the anti-mycobacterial extract can be obtained by alternative extraction solvents and that a methylene chloride extract produces a more pure active fraction.

In a preliminary step which might indicate the likelihood of purifying an active compound from of *Mammea Americana, Merchantia polymorpha*, and *Callistemon citrinus*, an extraction with alternative organic solvents was undertaken. If an extract with anti-mycobacterial activity by extraction with alternative organic solvents can be obtained, it would increase the likelihood that the active component is a single compound or a very small group of compounds which could be isolated as a pure fraction. The alternative solvent tested was methylene chloride.

About 5 gm of powdered leaf tissue was extracted in 100 ml absolute methylene chloride by shaking for 4 hrs. at room temp. The extracted material was tested by agar diffusion assay, generally as described above for tests with ethanol extracts. The methylene chloride extract demonstrated measurable and reproducible anti-mycobacterial activity against *M. smegmatis* 607 (ATCC).

Tables 2, 3, and 4 present side-by-side the major ingredients in ethanol extracts and methylene chloride extracts of *Mammea Americana, Merchantia polymorpha*, and *Callistemon citrinus*, respectively, as determined by Gas Chromatography/Mass Spectroscopy (GC/MS) analysis. The ethanol extraction was more effective in the retention of soluble material as indicated by the weight of the extracted material. In percentage of weight of starting material, the ethanol extraction yielded 18.7%, 1.6%, and 24.2%, while the methylene chloride yielded 1.46%, 0.26%, and 0.73% of *Mammea Americana, Merchantia polymorpha*, and *Callistemon citrinus*, respectively. Furthermore, as can be observed from the side-by-side listing of the compounds identified by GC/MS in Tables 2-4, there are fewer compounds in the methylene chloride extracts. Therefore, the active compound appears to be more pure when isolated by methylene chloride extraction.

TABLE 2

COMPOUNDS IN *MAMMEA AMERICANA* IDENTIFIED BY GAS CHROMATOGRAPHY/MASS SPECTROSCOPY

| METHYLENE CHLORIDE EXTRACT | ETHANOL EXTRACT |
|---|---|
| Glycol derivative | Acetic Acid |
| Hexanediol | Ethyl Acrolein |
| Glycol ether | 4,4-Pyran-4-one,2,3-dihydro-3,5-dihydroxy-5-methyl |
| Caryophyllene, Alpha and Beta | 1,2 benzenediol |
| Terpene | Copaene (Convallatoxinin, a sugar derivative) |
| Caryophyllene Oxide | 2-Furancarboxyldehyde-5-(hydroxymethyl) |
| Diphenylsulfide | Pyrogallic Acid (1,2,3 Benzenetriol) |
| Several high MW compounds. | Caryophyllene, Alpha and Beta |
| | 1,6,10-Dodecatriene-7,11-dimethyl-3-methylene |
| | m-Salicilic Acid |
| | Terpene |
| | Caryophyllene Oxide |
| | 1-H-Inden-1-one-octahydro-R-(−)3,7-Dimethyl-1,6-Octadiene |
| | 6-Octene-1-ol, 3,7-dimethyl-R isomers |
| | Pentadecanoic Acid, 1,4-methyl, 1-methyl ester |
| | Cyclodecene |
| | Phytosteroids |

TABLE 3

COMPOUNDS IN *MERCHANTACEA POLYMORPHA* IDENTIFIED BY GAS CHROMATOGRAPHY/MASS SPECTROSCOPY

| METHYLENE CHLORIDE EXTRACT | ETHANOL EXTRACT | |
|---|---|---|
| Beta-myrcene | 2-Propylamine | 2,3 Nonadiene |
| Hexalecanoic acid | Phenylpropanol Amine | Caryophyllene Oxide |
| | Acetic Acid | 2-Pentganol, 2-methyl-Salicilic Acid |
| | Terpene | 1 -Hexane |
| | Dodecane | Octadecene |
| | Acetaldehyde | 1.6-Heptadiene-2,5-dimethyl |
| | Cyclopropylcarbinol | Bicyclo-3.1.1-heptane-2,6,6-trimethyl |
| | 1-Nonanol | Cyclodecene |
| | Cyanoacetamide | Propyl nitrile-3-methylamine |

TABLE 3-continued

COMPOUNDS IN *MERCHANTACEA POLYMORPHA* IDENTIFIED BY GAS CHROMATOGRAPHY/MASS SPECTROSCOPY

| METHYLENE CHLORIDE EXTRACT | ETHANOL EXTRACT |
|---|---|
| | Hexdecanal | 6-Octene-1-ol, 3,7-dimethyl-R isomers |
| | Butyl Urea | Tetradecanal, Octadecanal |
| | Caryophyllene, Alpha and Beta | 1,6,10-docecatriene- |
| | Tetradecanal | Dodecanal |
| | 2-(5 H) Furanone, 5-ethyl | Oleic Acid |
| | Docapal | 7,11-Dimethyl-3-methylene |
| | R-(−)3,7-Dimethyl-1,6-Octadiene | Methyl Heptanol |
| | Phytosterols | Propenamide |

TABLE 4

COMPOUNDS IN *CALLISTEMON CITRINUS* IDENTIFIED BY GAS CHROMATOGRAPHY/MASS SPECTROSCOPY

| METHYLENE CHLORIDE EXTRACT | ETHANOL EXTRACT |
|---|---|
| Alpha Pinene | Acetic Acid |
| Alpha Phillandrene | Furfural |
| Octadiene | Alpha Pinene |
| 1-Benzene (1-Me-2(1-Methylethyl) | 1,6-Octadiene-3-ol,3,7-dimethyl |
| Eucalyptol | 3-Cyclohexene-1-methanol |
| 1,6-Octadiene-3,5-dimethyl (trans) | 1,2.3-Benztriol (Pyrogallol) |
| 3-Cyclohexene-1-methanol | Gluco derivative |
| Bicyclo-7.2.0-undec-4-one-4.11.11-trime | Sugar derivative |
| Camphene | 9-Eicosane |
| 1,4-Cycloprop-azulene | Benzyl derivative |
| Terpene | Bicyclo-{3.3.3.}-Heptane 6,6-dimethyl 2 methylene |
| Phytol | Gamma-Sitrosterol |
| 5-Octadecene | Phosphoric acid, dioctyldecyl ester |
| 3-Carene | Ethoxy-1-propanol |
| Vitamin E | Vinyl Crotonate |
| | Bicyclo-{3.1.1}hex-2-ene-2-methyl-5-(1-methylethyl) |
| | Furancarboxaldehyde |
| | 1(H)-Cycloprop-azulene-decahydro-1,1,7 |
| | Purine derivative |
| | Terpene derivative |
| | Cyclooctene-3-ethenyl |
| | Alpha Pinene |
| | Naphthylene derivative |
| | Vitamin E |
| | Phytol |
| | Phytosteroids |

EXAMPLE 4

This example demonstrates that the *Mammea Americana, Merchantia polymorpha*, and *Callistemon citrinus* plant extracts can be purified into fractions having an increased anti-mycobacterial activity.

It is noteworthy from Tables 2-4 that the ethanol and methylene chloride fractions contain few compounds in common. This suggests that the active compound(s) may be a minor component of the extract and not easily discernable when a total GC/MS is performed. If the anti-mycobacterial compound(s) can be separated into a fraction containing yet fewer components, it may be possible to isolate a larger quantity of the active fraction which would be subject to renewed GC/MS analysis to identify the active compound of each plant of the invention.

Figure 2:
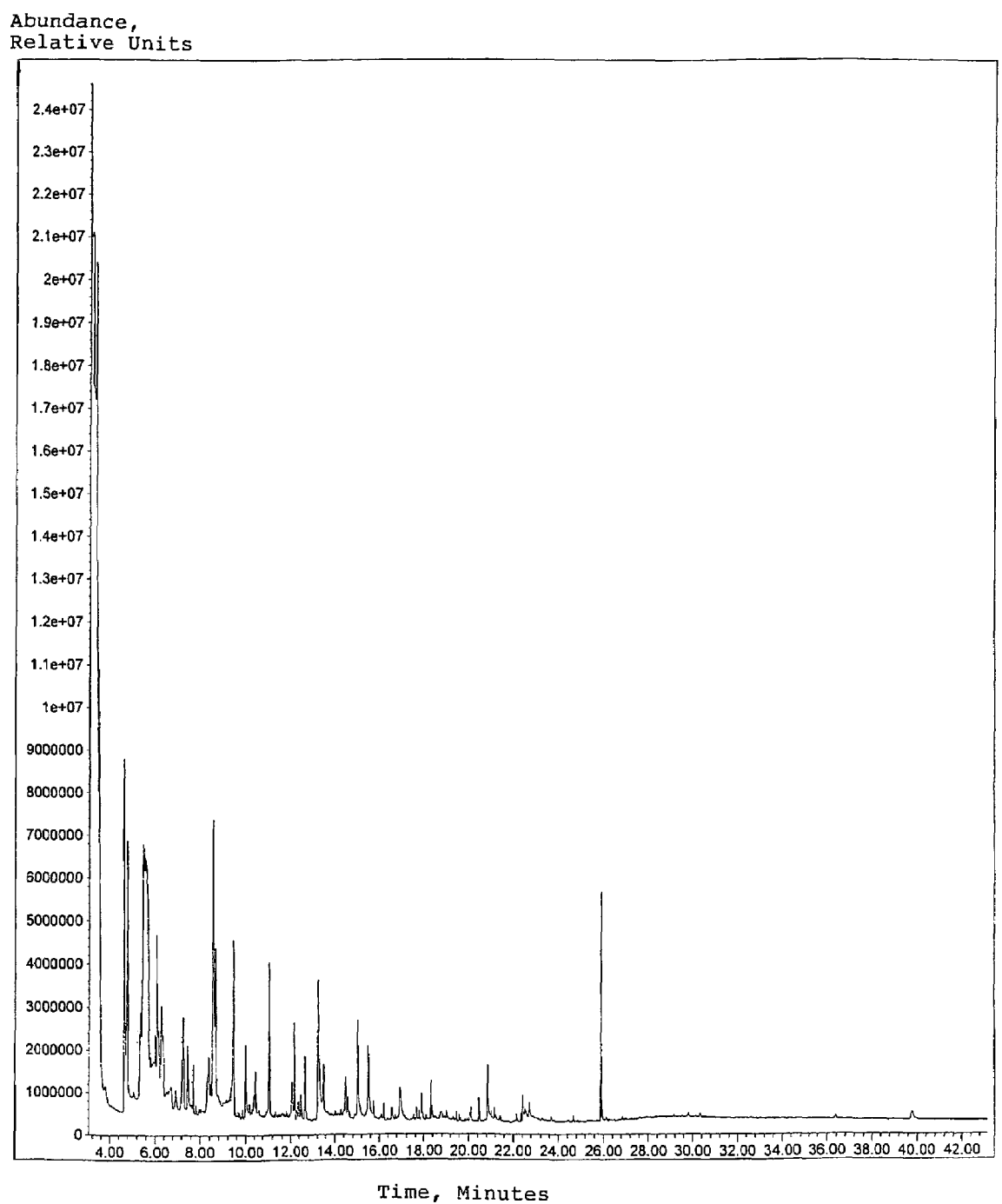
FIG. 2 is a Gas Mass/Mass Spectroscopy (GC/MS) analysis of an active fraction of *Marchantaceae polymorpha*. The material was prepared by combination of 8 HPLC runs, concentrated to 1 drop to which about 0.3 ml methanol was added. 10 .mu.l were analyzed on GC/MS. The peaks were identified. The peak at 13 minutes is cobaltocene, 1,1',2,2',3, 3',4,4'-octamethyl.
Figure 3:
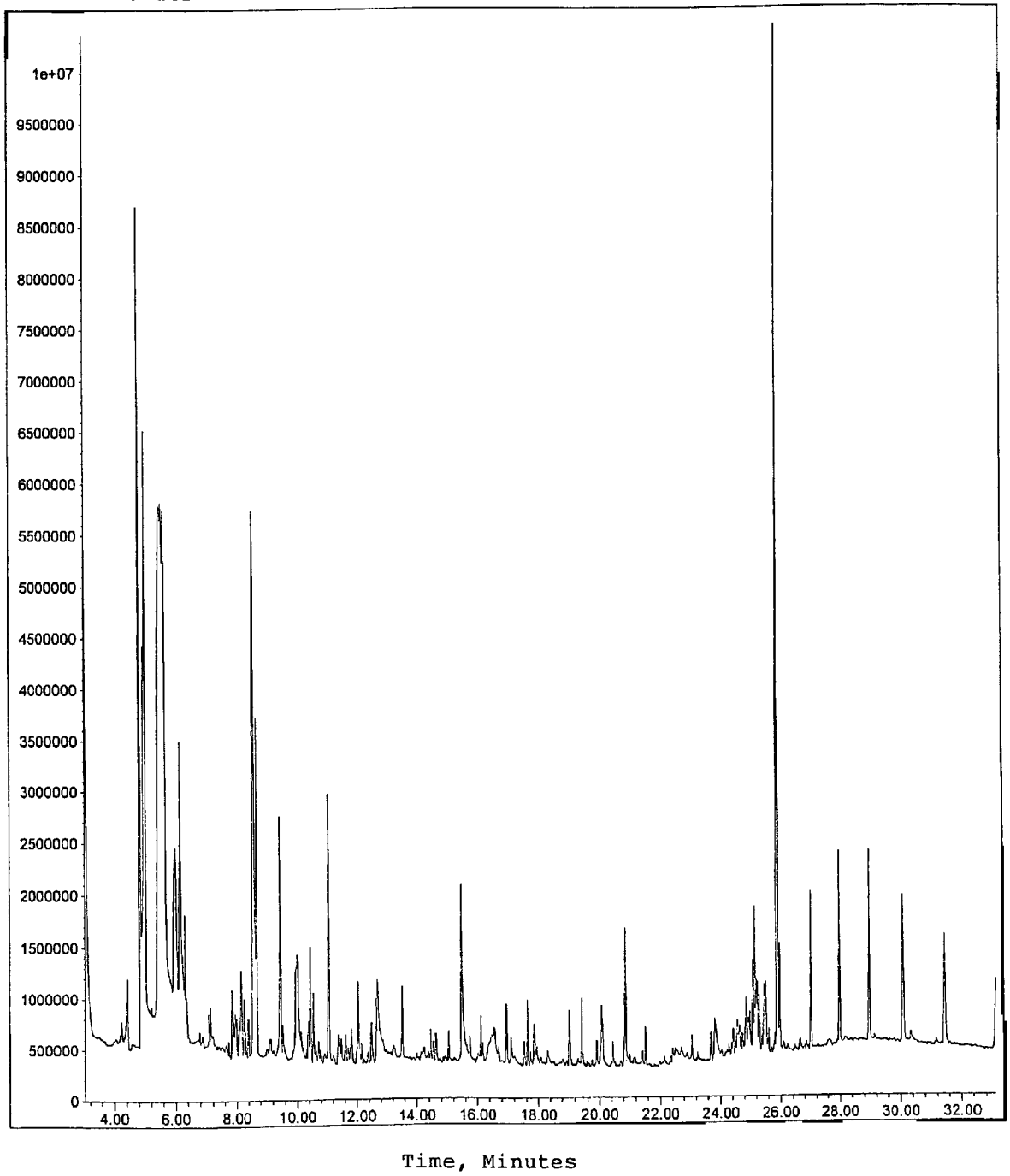
FIG. 3 is a Gas Mass/Mass Spectroscopy (GC/MS) analysis of an active fraction of *Callistemon citrinus*. The material was prepared by combination of 4 HPLC runs, concentrated to 1 drop to which about 0.3 ml methanol was added. 10 μl were analyzed on GC/MS. The peaks were identified. The peak just before 20 minutes is galoxolide, followed by a peak comprising benzyl salicylate.

An HPLC separation and isolation of an active fraction was attempted. High Pressure Liquid Chromatography (HPLC) was performed using a Discovery RP-Amide C-16 Column, 15 cm long, 4.6 mm wide (Supelco, Bellefort, Pa.). An isocratic, i.e. steady concentration, of a polar solvent phase was used. The solvent phase consisted of dilute phosphoric acid in methanol. The flow rate was 2 ml/minute. Therefore exit is dependent on MW (larger MW exists later) and polarity. The more polar the compound, the quicker it solubilizes into the solvent, but it is retained longer in the static phase of the column which holds back the more polar compounds. The fractions were monitored by UV, at 254 nm wave-length. One to three fraction per plant extract were collected at the indicated times. As can be seen from Table 5, individual fractions having strong activities against *E. coli* and against *M. smegmatis* were identified and GC/MS analysis identified the compounds present in these fractions. See, for example, FIGS. 1-3. Based on consideration of the relative polarity and molecular weights of the compounds identified for the respective plants in the total methylene chloride extract, the compounds in the right-most column of table 5 "Additional Compounds" lists compounds which are not observed in the active fraction of the extract of the respective plants, but which are likely to be present in smaller quantities ("trace amounts") in the active fraction and which might contribute to the anti-mycobacterial activity.

It has been demonstrated now that an active, purified fraction and individual compounds can be isolated and identified as the active compounds of plant extracts having anti-mycobacterial activity.

TABLE 5

SUMMARY OF FRACTIONATION, ZOI AND GC/MS FINDINGS REGARDING ANTI-MICROBIAL COMPOUNDS/FRACTIONS

| | HPLC Fractions | Fraction Range* | *E-Coli* 25922 ZOI (mm) | *M. Smegmatis* ATCC 607 ZOI (mm) | Compounds Identified in Fraction | Additional Compounds |
|---|---|---|---|---|---|---|
| *Mammea Americana* L.C. (*Guttiferacea*) | 1 | 0-2.5 min. | 8 | 8 | | |
| | 2 | 3.0-5.0 min. | 13 | 10 | Acetic acid, cobaltocene-octamethyl Stigmastan-3,5-diene, | α-caryophylene; β-caryophelene; caryophelene oxide; |

TABLE 5-continued

SUMMARY OF FRACTIONATION, ZOI AND GC/MS FINDINGS
REGARDING ANTI-MICROBIAL COMPOUNDS/FRACTIONS

| | HPLC Fractions | Fraction Range* | E-Coli 25922 ZOI (mm) | M. Smegmatis ATCC 607 ZOI (mm) | Compounds Identified in Fraction | Additional Compounds |
|---|---|---|---|---|---|---|
| | | | | | friedelin, terpene | cyclododecaine |
| Marchantaceae polymorpha L.C. (Marchantaceae) | 1 | 0-1.5 min. | 14 | 13 | Acetic acid, Cobaltocene-octamethyl β-myrceane | Hexadecanoic acid |
| | 2 | Insufficient | | | | |
| Callistemon citrinus (Curtis) Skeels (Myrtaceae) | 1 | 0-1.25 min. | 8 | 6 | | |
| | 2 | 1.25-2.7 min. | 12 | 8 | | |
| | 3 | 4.0-5.0 min. | 13 | 12 | Acetic acid Galoxilide Benzyl salicylate Terpene Eucalyptol α-pinene | 3-cyclohexane-1-methanol camphene 1,4-cycloprop-azulene phytol |
| Streptomycin** | | | 14 | 17 | | |

*Based on retention times.
**Control consists of 10 micrograms streptomycin in the same solvent as the sample on the same 6 mm disc.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is' incorporated into the specification as if it were individually recited herein. The word "about," when accompanying a numerical value, is to be construed as indicating a deviation of up to and inclusive of 10% from the stated numerical value. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A pharmaceutical composition consisting of cobaltocene-octamethyl and stigmastan-3,5,-diene.

2. A pharmaceutical composition consisting of cobaltocene -octamethyl, stigmastan-3,5,-diene, and an additional compound selected from the group consisting of α-caryophylene, μ-caryophelene, caryophylene oxide, friedelin, cyclododecaine, acetic acid, terpene, and mixtures thereof.

3. The pharmaceutical composition of claim 2, where the additional compound is friedelin.

4. The pharmaceutical composition of claim 2, where the additional compound is terpene.

5. A pharmaceutical composition consisting of a pharmaceutical carrier, cobaltocene-octamethyl and stigmastan-3,5,-diene.

6. A pharmaceutical composition consisting of cobaltocene -octamethyl, stigmastan-3,5,-diene, a pharmaceutical carrier and an additional compound selected from the group consisting of α-caryophylene, μ-caryophylene, caryophylene oxide, friedelin, cyclododecaine, acetic acid, terpene, and mixtures thereof.

7. The pharmaceutical composition of claim 6, where the additional compound is friedelin.

8. The pharmaceutical composition of claim 6, where the additional compound is terpene.

9. The pharmaceutical composition of any one of claims 1-8 wherein said cobaltocene octamethyl is cobaltocene 1, 1', 2, 2', 3, 3', 4, 4'-octamethyl.

* * * * *